(12) United States Patent
Moser et al.

(10) Patent No.: US 9,938,971 B2
(45) Date of Patent: Apr. 10, 2018

(54) SELF-LOCKING COUPLING BETWEEN A PUMP CASING AND A PUMP MODULE

(71) Applicant: Medaxis AG, Baar (CH)

(72) Inventors: Beat Moser, Uerzlikon (CH); Adrian Zweifel, Jona (CH); Beat Widmer, Luzern (CH); Martin Butler, Hohenrain (CH); Lukas Christen, Luzern (CH); Roman Good, Zurich (CH); Daniel Napoletano, Eglisau (CH)

(73) Assignee: Medaxis AG, Baar (CH)

( * ) Notice: Subject to any disclaimer, the term of this patent is extended or adjusted under 35 U.S.C. 154(b) by 0 days.

(21) Appl. No.: 15/272,069

(22) Filed: Sep. 21, 2016

(65) Prior Publication Data

US 2017/0080144 A1 Mar. 23, 2017

(30) Foreign Application Priority Data

Sep. 23, 2015 (EP) .................................... 15186573

(51) Int. Cl.
*F04B 53/22* (2006.01)
*F04B 17/03* (2006.01)
(Continued)

(52) U.S. Cl.
CPC .......... *F04B 53/22* (2013.01); *A61B 17/3203* (2013.01); *F04B 9/047* (2013.01);
(Continued)

(58) Field of Classification Search
CPC .. F04B 19/22; F04B 53/22; F04B 1/00; F04B 23/023; F04B 39/0022; F04B 53/144;
(Continued)

(56) References Cited

U.S. PATENT DOCUMENTS

| 5,667,141 A | * | 9/1997 | Suttner | .................. B08B 3/026 239/332 |
| 6,032,349 A | * | 3/2000 | Wagner | .................. F16B 21/09 29/464 |
| 7,553,318 B2 | | 6/2009 | Ammann | |

(Continued)

FOREIGN PATENT DOCUMENTS

| EP | 1296601 B1 | 8/2006 |
| EP | 1924305 B1 | 2/2010 |

(Continued)

*Primary Examiner* — Bryan Lettman
*Assistant Examiner* — Timothy Solak
(74) *Attorney, Agent, or Firm* — Fishman Stewart PLLC (57) ABSTRACT

A device for producing a fluid jet suitable for hygienic requirements in mechanical wound cleaning, including removal of biological tissue, may include a drive casing with a drive and a pump module with a pump casing which can be detachably joined. The drive casing may include a positive-locking element and the pump casing may include a positive-locking counter-element. The positive-locking element may interact with the positive-locking counter-element so that the pump casing is imposed a pivotal motion relative to the drive casing until reaching a final position. In final position the pump casing may be connected to the drive casing and a drive element may be connected to an associated drive counter-element. Drive element and drive counter-element may be arranged eccentric to a pivot axis of the pivotal motion and may be formed so a positive-locking connection arises between the drive element and drive counter-element due to the pivotal motion.

10 Claims, 9 Drawing Sheets

(51) Int. Cl.
   *F04B 9/04* (2006.01)
   *F04B 53/14* (2006.01)
   *F04B 19/22* (2006.01)
   *A61B 17/3203* (2006.01)
   *A61B 90/98* (2016.01)

(52) U.S. Cl.
   CPC .............. *F04B 17/03* (2013.01); *F04B 19/22* (2013.01); *F04B 53/147* (2013.01); *A61B 90/98* (2016.02)

(58) Field of Classification Search
   CPC ...... F04B 53/146; F04B 53/147; F04B 90/47; F04B 19/04; F04B 9/047
   See application file for complete search history.

(56) References Cited

U.S. PATENT DOCUMENTS

| | | | |
|---|---|---|---|
| 8,177,524 B1 * | 5/2012 | Kieffer | F04B 17/03 417/360 |
| 2001/0002562 A1 | 6/2001 | Moutafis et al. | |
| 2002/0176788 A1 | 11/2002 | Moutafis et al. | |
| 2007/0286754 A1 * | 12/2007 | Laing | F04D 29/426 417/423.14 |
| 2008/0202507 A1 | 8/2008 | Brandli | |
| 2008/0221602 A1 | 9/2008 | Kuehner et al. | |
| 2009/0242470 A1 * | 10/2009 | Muenkel | B01D 35/30 210/148 |
| 2010/0049228 A1 | 2/2010 | Kuehner et al. | |
| 2011/0150680 A1 | 6/2011 | Dion et al. | |
| 2012/0051956 A1 * | 3/2012 | Grip | A61M 5/1413 417/413.1 |
| 2014/0079580 A1 | 3/2014 | Habe | |
| 2014/0093406 A1 * | 4/2014 | Dorfler | F04B 53/16 417/395 |

FOREIGN PATENT DOCUMENTS

| | | |
|---|---|---|
| WO | WO-0197700 A2 | 12/2001 |
| WO | WO-2007031304 A1 | 3/2007 |

* cited by examiner

FIG. 10

SELF-LOCKING COUPLING BETWEEN A PUMP CASING AND A PUMP MODULE

CROSS-REFERENCE TO RELATED APPLICATION

This application claims the benefit of priority to European patent application No. 15186573.0, filed Sep. 23, 2015, which is incorporated herein by reference in its entirety as though fully set forth herein.

TECHNICAL FIELD

The present invention relates to a device for producing a fluid jet, in particular for the removal of biological tissue.

BACKGROUND

Devices for producing a water jet for the treatment of biological tissue are known from EP 1 924 305 131, WO 2007/031304 A1, U.S. Pat. No. 7,553,318 B2 and WO 01/97700 A2. The present invention in particular relates to the debridement by way of a water jet. With debridement, the wound is cleaned for promoting wound healing, also scab and overgrowths are commonly removed. The aforementioned publications show the efforts in the expert industry to propose solutions for performing this debridement by use of a water jet. Another document originating from the present applicant is given by EP 1 296 601 B1.

With equipment that is used in hospitals and in particular in the mechanical treatment of wounds, there is a need to form certain components used in the treatment with a fluid jet such that they are disposable products or can at least be sterilized. On the other hand, certain components of a device for producing a fluid jet, for example, at least the electric drive of a pump, can effectively not be sterilize and are also commonly too expensive to be designed as disposable products.

The present invention seeks to provide a device for producing a fluid jet which can be produced economically and in a simple manner while satisfying the above requirements.

BRIEF SUMMARY

To solve this problem, the present invention proposes a device having the features of claim 1. The device according to the invention has a drive casing in which a drive is provided. This is commonly an electrically powered drive. The drive casing accommodates this electric drive and usually comprises control elements for switching on and off and for actuating the drive. Furthermore, the device according to the invention has a pump module. This pump module comprises a pump casing as well as a mechanism within the pump casing which is adapted to pressurize and convey fluid supplied to the pump casing. The pump casing can comprise, for example, at least one piston communicating with inlet and outlet openings or the fluid so as to suck in said fluid at the inlet opening and discharge it at the outlet opening at an increased pressure. The pump casing can comprise valves for directed conveyance of the fluid. The pump casing itself can have a relatively simple design and be configured as a disposable member, in particular as a plastic member. Preferably all components of the pump module are designed to be made of plastic.

A modular design of the device is proposed with the present invention in which the pump casing on the one hand and the drive casing on the other hand can be detachably joined.

According to the invention, the drive casing has at least one positive-locking element. The pump casing has a positive-locking counter-element interacting with this positive-locking element when joining the pump casing and the drive casing. The positive-locking element and the positive-locking counter-element there interact until a final position is reached such that the pump casing is imposed a pivotal motion relative to the drive casing until the pump casing has reached its final position. The final position of the pump casing is that position in which the pump casing is connected to the drive casing and at least one drive element of the drive provided, on the drive casing is connected to an associated drive counter-element of the pump module. The drive element and the drive counter-element are there arranged eccentric to a pivot axis of a pivotal motion that is imposed to the pump module relative to the drive casing when joining the drive and the pump module. The configuration of the drive element and the drive counter-element is such that a positive-locking connection between the drive element and drive counter-element arises due to the pivotal motion imposed until the final position has been reached.

It is with the present invention ensured that joining the pump module and the drive necessarily results in a positive-locking connection of the respective elements for driving the pump. The drive element is there coupled to the drive, while the drive counter-element is regularly connected directly or indirectly to a piston which pressurizes the fluid in a cylinder of the pump module.

The device according to the invention can therefore be easily handled. Even without technical expertise, joining the drive casing and the pump module results in the two drive elements of the device necessarily being drivingly coupled and accordingly being in operative connection to each other. The guidance between the drive casing and the pump module effected by the positive-locking element and the positive-locking counter-element there prevents incorrect operation.

The positive-locking element and the positive-locking counter-element preferably form a bayonet lock which first imposes an axial motion upon the pump casing that is relative to the drive casing. This axial motion is an axial motion relative to a substantially cylindrical recess. At the end of this axial motion, a pivotal relative motion is imposed by interaction of the positive-locking element and the positive-locking counter-element and extends substantially perpendicular to the axial motion. It is by the second part of the pivotal motion, which is determined by the bayonet lock, also ensured that the connection between the pump module and the drive casing is secured. Catch mechanisms or projections common for bayonet locks can there be provided which prevent accidental reverse rotation of the pump module relative to the drive casing. In the embodiment presently discussed, the recess can be defined by the pump casing in which a projection of the drive casing engages. However, it is in view of a compact design preferable to provide the recess on the drive casing. The drive element is there preferably exposed in the recess, however, is preferably received within the recess. The drive element accordingly usually does not project beyond the recess in the longitudinal direction, which is usually the direction of movement of the drive element, toward the exterior. In this embodiment, the pump module is configured such that the pump casing is at least in part insertable into the recess.

According to a preferably embodiment of the present invention, the pump casing has a recess in which the drive counter-element is exposed. For insertion into a recess formed in the drive casing, the pump casing preferably comprises a sleeve section which encloses the drive counter-element and forms the positive-locking counter-element. Also in this embodiment, a drive counter-element is at least predominantly with its outwardly exposed connection end located within the recess, which is hereinafter referred to as the pump recess, so that this connection end of the drive counter-element, though being protected within the pump casing, is also exposed within the pump casing.

According to a preferable embodiment of the present invention, the recess and/or the pump casing is/are at least in part designed to be rotationally symmetrical. The rotationally symmetrical design pertains in particular to an enveloping surface, for example, at inner circumferential surface sections of the recess and/or outer circumferential sections in particular of the sleeve section of the pump casing. The positive-locking elements or the positive-locking counter-elements are commonly within or outside this enveloping surface. The rotationally symmetrical configuration gives rise to guide surfaces which guide at least the axial motion when joining the pump module and the drive casing. This axial motion is commonly a motion that is directed parallel to the center longitudinal axis of the recess or of a substantially cylindrical sleeve section, respectively. While the rotationally symmetrical enveloping surface performs the axial motion, the interaction of the positive-locking element and positive-locking counter-element indeed also causes axial guidance, but in particular forced guidance of the pivotal motion until the final position has been reached.

According to a preferred embodiment of the present invention, the positive-locking element and the positive-locking counter-element form a guide that during joining defines a unique orientation of the pump casing relative to the drive casing. A configuration may be provided which fulfills a poka-yoke function and thereby defines that the pump casing can be joined in only a single position, possibly in two positions rotated by 180°, relative to the drive casing due to the interaction of the positive-locking and the positive-locking counter-element. Several positive-locking elements and positive-locking counter-elements can be provided on the circumference of the recess and/or a sleeve section and each can be assigned exactly to each other so that the respectively associated pairs of positive-locking elements and positive-locking counter-elements necessarily must be made to overlap in order to enable joining the pump module with the drive casing. This configuration may reliably prevent faulty joining of the pump casing and the drive casing and thereby prevent inadequate mechanical coupling of the drive element and drive counter-element.

According to a preferred development of the present invention, the positive-locking element and the positive-locking counter-element are configured such that the pump casing when joining and at the end of the axial motion is pivotable relative to the drive casing by an angle of between 10° and 90°, preferably by an angle of 25-35°, i.e. 30°+/−5°. Such pivotability can usually be achieved by the user without the hand holding the pump casing changing the grip and is thereby realized in a comfortable manner. The joining action can thereby be performed comfortably and with one hand.

According to a preferred embodiment of the present invention, the drive element is a drive pusher. The drive counter-element is preferably formed integrally as part of a pump piston. In other words, the drive counter-element is formed by the pump piston. It is understood that the part of the piston in a cylinder used for pumping is commonly accommodated inside the pump casing, whereas the other free end of the pump piston on the drive side forms the drive counter-element. The guide formed by the drive element and the pump piston between the pump module and the drive casing is in the axial direction there configured such that the drive element abuts an abutment surface of the pump piston before the final position has been reached. This configuration ensures that the drive element and the drive counter-element after joining the pump casing and the drive casing bear against each other in the axial direction. The drive pusher with its abutment surface there preferably bears against the counter-surface of the pump piston before joining the drive casing and the pump module in the axial direction has been completed. In other words, the abutment surface during, axial joining, strikes against the counter-surface. The drive element and the drive counter-element thereby at least at the face sides bear against each other. This bearing is achieved at least when the final position has been reached. This bearing can preferably also be effected prior to the final position being reached. The remaining axial displacement motion between the pump module and the drive casing is then compensated by an axial relative motion of the pump piston and/or the drive pusher so that the relative position of the drive element and the drive counter-element does not change despite an axial joining motion. This increases security so that the drive element at the end of the axial joining motion at the end side securely bears against the pump piston.

For simplifying the configuration, the drive piston is commonly on the drive side held axially immovable, whereas the drive counter-element associated with the pump module is mounted axially displaceable.

In view of the forced positive-locking connection due to a pivotal motion between the pump casing and the drive casing taught by the invention, it is in a preferred embodiment of the present invention proposed that the drive element or the drive counter-element comprise a hammerhead and the respectively other of the two elements an adapted hammerhead seat for engaging over the hammerhead. The hammerhead seat is there matched to the configuration of the hammerhead such that the pivotal motion at the end of the joining motion, i.e. after completion of the relative axial motion and in the framework of the pivotal motion, leads to the hammerhead seat in a positive-locking manner engaging over the hammerhead, and both elements of the drive are thereby connected to each other on both sides in the axial direction in a positive-locking manner. An alternating axial motion of the drive element thereby necessarily also leads to a corresponding alternating motion of the drive counter-element after the pump module has reached the final position and the drive has been switched on.

It is in view of exact axial coupling by way of a positive-locking connection of the drive element and drive counter-element according to a preferred development of the present invention proposed to provide the element forming the hammerhead seat in a rotationally fixed manner. The element forming the hammerhead seat can be rotatably supported and in particular when the hammerhead itself is formed rotationally symmetrical so that its orientation relative to the hammerhead seat does not affect the quality of the positive-locking connection to be produced in the context of the joining.

To further increase security against incorrect joining, it is according to a further preferred development of the present invention proposed to provide the hammerhead seat with a claw engaging over the hammerhead. The claw engaging over the hammerhead there causes axial fixation of the drive element and the drive counter-element. Fixation within this meaning, however, can also be understood to be a configuration in which a cyclic axial motion of the drive element is at times not completely transferred to the drive counter-element, as both allow for a certain axial play. Any such play leading to the two elements knocking, however. Which results in undesirable noise and wear in particular with a high-frequency drive, is to be avoided. The hammerhead seat is usually designed such that it receives the hammerhead within itself substantially without axial play. According to the preferred development presently discussed, however, the claw being provided according to the embodiment also forms a stop. This stop is effective before the final position has been reached and interacts with the hammerhead provided that the latter is located at the same height as the claw in such a way that pivoting is in the final position prevented. In other words, the interaction of the hammerhead and the stop prevents the final position from being reached. The stop acts in a pivoting motion of the pump module relative to the drive casing, thereafter it acts radially.

A drive device of the previously discussed device for producing a fluid jet is protected in an independent claim. According thereto, the drive unit has a drive which is provided in a drive casing. The drive casing comprises at least one positive-locking element with which the pump module previously mentioned can be affixed to the drive casing. The fixation is performed in a positive-locking manner, preferably in the manner described above by way of a bayonet lock. The drive casing is further provided with a recess. Exposed in this recess is a drive element of the drive. The drive element is arranged eccentric relative to a center longitudinal axis of the recess. Since the recess of the drive casing allows the pump module to be at least partially inserted into the recess to pivot, the recess is commonly formed with a rotationally symmetrical inner circumferential surface. The same applies to the portion of the pump module introduced into the recess. This portion is commonly formed as a cylindrical section having a circular outer circumferential surface. With such a configuration, it is possible to insert the pump module at least in part into the recess of the drive casing and to connect it in a positive-locking manner by pivoting.

The drive element comprises a positive-locking mechanism for the positive-locking connection of the drive element to a drive counter-element of the pump module by pivoting the pump module about the center longitudinal axis. The positive-locking mechanism is formed such that the drive element of the drive unit is connected to a drive counter-element of the pump module when pivoting the pump module about the center longitudinal axis of the recess for positive-locking fixation of the pump module at the drive casing by way of the positive-locking element. In the pump module according to the invention, the preferably positive-locking counter-element for fixation of the pump module at the drive casing and the positive-locking mechanism for connecting the drive element and the drive counter-element are accordingly each located eccentric to the center longitudinal axis of the recess. The drive unit according to the invention provides the possibility of forced coupling of both the pump module as a whole as well as the drive element of the drive unit to the associated drive counter-element of the pump module by an even pivotal motion.

The pump module of the previously discussed device for producing a fluid jet specified in a further independent claim is also by itself considered as being essential to the invention. This pump module has a pump casing with at least one positive-locking counter-element with which the pump module can be fixed at a drive casing of a drive. The pump casing is further configured as being adapted for the insertion into a recess of the drive casing and for this purpose has a corresponding cylindrical section. The cylindrical section is typically formed with a rotationally symmetrical outer circumferential surface and in the manner of a fitting adapted to the dimension of the recess. The pump module further has a drive counter-element which is disposed eccentric to a center longitudinal axis of the cylindrical section. The drive counter-element is provided with a positive-locking counter-mechanism for coupling the drive counter-element to a drive element of the drive exposed in the recess in a positive-locking manner by pivoting the pump module about the center longitudinal axis of the cylindrical section. This pivotal motion takes place during the positive locking fixation of the pump module to the drive casing by way of the positive-locking element of the pump casing.

BRIEF DESCRIPTION OF THE DRAWINGS

Please gather further details and advantages of the present invention from the following description of an embodiment in combination with the drawing, in which.

DETAILED DESCRIPTION

Figure 1:
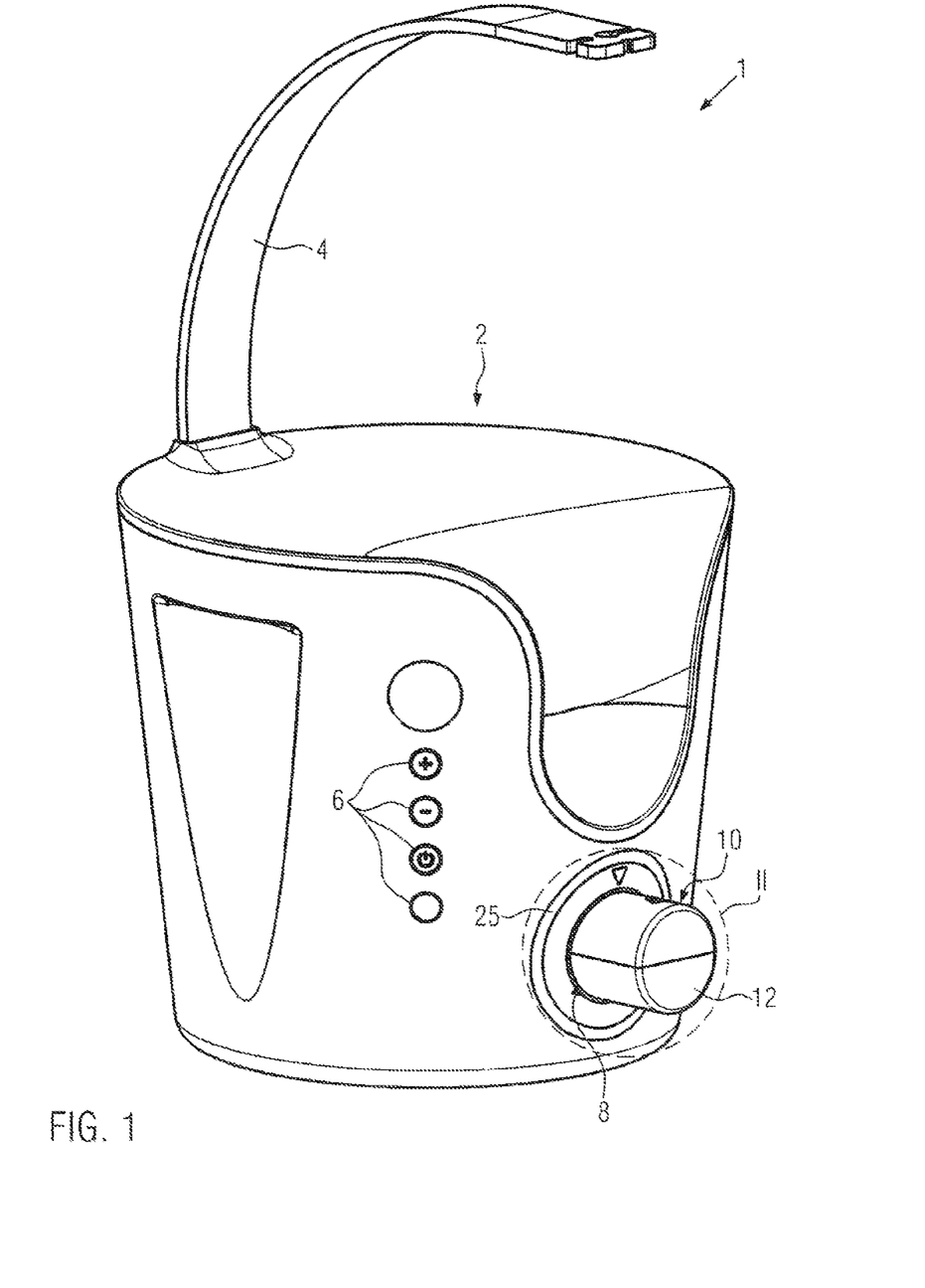
FIG. 1 shows a perspective view of an embodiment of a device for producing fluid jet.
Figure 2:
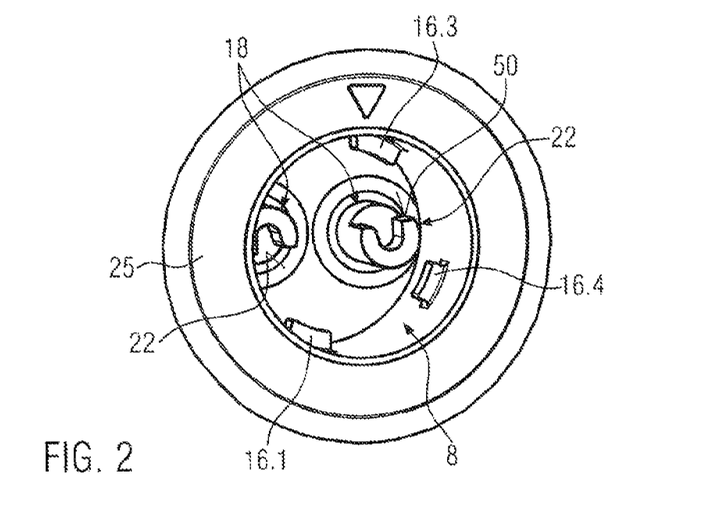
FIG. 2 shows the detail of FIG. 1 in an enlarged representation without the pump module.
Figure 3:
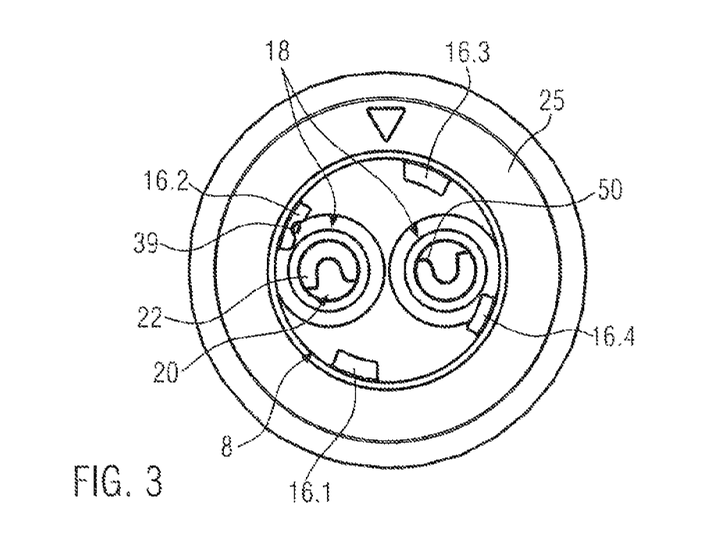
FIG. 3 shows the detail of FIG. 2 in a top view.

FIG. 1 shows a perspective side view of an embodiment of a drive unit 1 with a drive provided in a drive casing 2 which is an electric drive. A holder 4 protrudes from drive casing 2 for holding a fluid bag. Exposed on drive casing 2 are also various control elements 6 which serve to actuate the drive and to switch the drive on and off. Reference numeral 8 denotes a substantially cylindrical recess in which a pump module designated with reference numeral 10 is inserted and which projects beyond recess 8. Pump module 10 comprises a pump casing 12 composed of two casing shells. As illustrated in FIGS. 2, and 3, drive casing 2 has lugs 16 that protrude inwardly into recess 8 and are embodiments of positive-locking elements of the present invention. Four lugs 16 are presently provided distributed on the circumference. The lug identified by reference numeral 16.4 has a smaller radial extension and a smaller extension in the circumferential direction than the other lugs 16.1 to 16.3. Exposed in recess 8 are further drive elements in the form of drive pushers 18 which are connected to the drive provided within drive casing 2 and driven cyclically to and fro in the longitudinal direction. Drive pushers 18 form an abutment surface 20. Two drive pushers 18 are presently provided. A C-shaped claw 22 in a top view projects over abutment surface 20 and forms a hammerhead seat 24 between itself and abutment surface 20. The respective details are clearly marked in particular in FIG. 8*a*.

A seal made of rubber-elastic material is in FIGS. 1 and 2 marked with reference numeral 25 and extends between the outer side of drive casing 2 and an opening toward the recess. Recess 8 is formed by a cup that is associated with the drive and encloses both drive pushers 18. This cup is subjected to certain vibrations that are caused by the drive. Seal 25 prevents direct transmission of these vibrations to drive casing 2.

Figure 4:
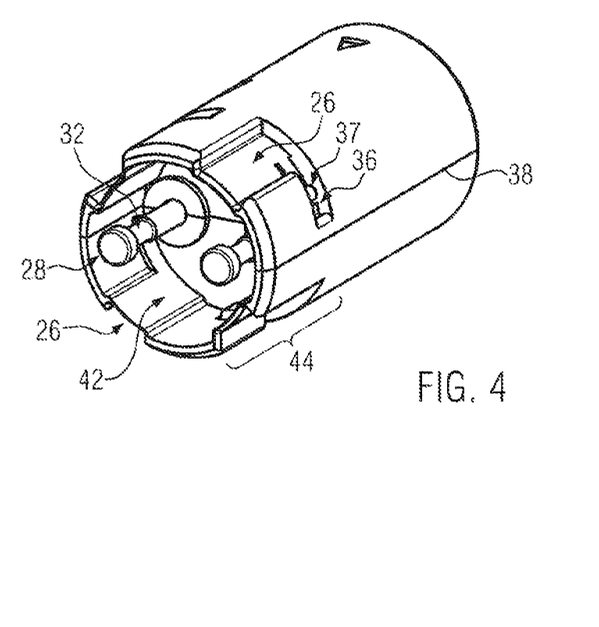
FIG. 4 shows a top perspective view of an end portion of the pump module shown in FIG. 1.
Figure 5:
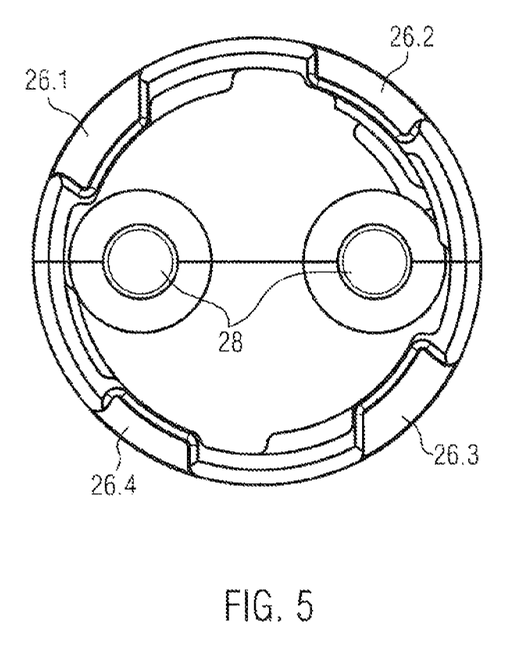
FIG. 5 shows an face side top view of the end portion shown in FIG. 4.
Figure 6A:
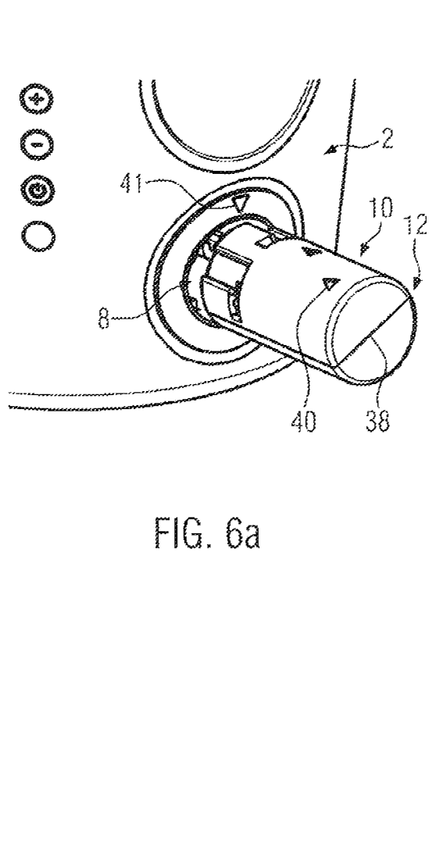
FIGS. 6a-c show a sequence of steps for joining the pump module.
Figure 6B:
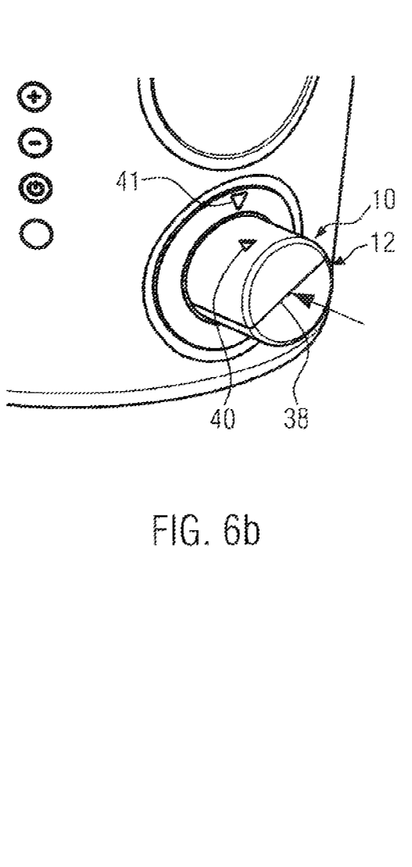
Figure 9A:
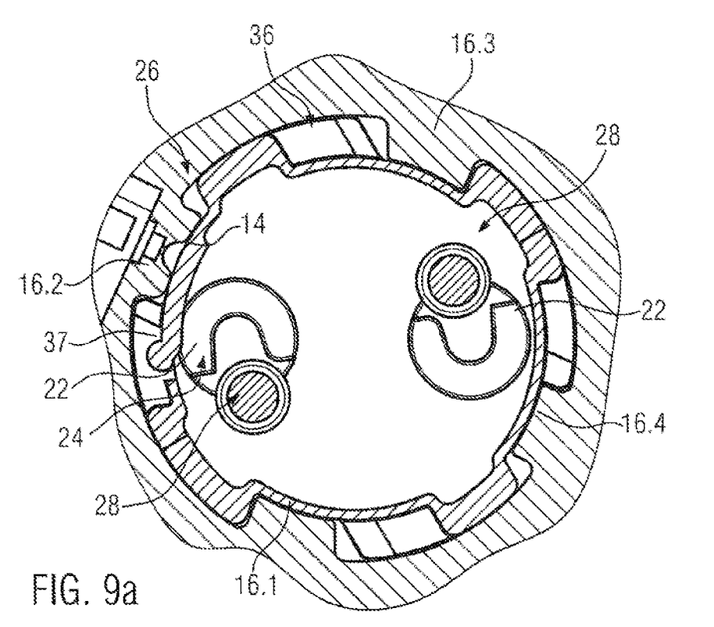
FIG. 9a-c show partially sectional top views of the interacting ends of the drive element and the drive counter-element and their relative position when pivoting during the joining process.

As is shown in particular in FIGS. 4 and 5, pump module 10 comprises grooves 26 that are marked with reference numeral 26 and extend in the axial direction relative to cylindrical pump casing 12 and which by way of example form positive-locking counter-elements within the meaning of the present invention. These grooves 26 are provided on the outer circumference of pump casing 21 strictly extending in the axial direction. The groove marked with reference numeral 26.4 has a smaller radial depth and a smaller width in the circumferential direction and is formed adapted for precise reception of the smaller lug 16.4. Due to the interaction of in particular smaller lug 16.4 with smaller groove 26.4, a biunique orientation of pump casing 12 is defined during joining, i.e. when inserting pump casing 12 into recess 8. Pump casing 12 can be inserted only at an angle perpendicular to a final position offset by 30 shown in FIG. 6*c*. This pivoted position is illustrated in FIGS. 6*b* and 9*a*. Reference numerals 28 in FIG. 9*a* there illustrate two hammerheads which are provided at free ends of each one pump piston 30 and each form an embodiment of a drive counter-element within the meaning of the present invention. Hammerhead 28 projects beyond an end-side cylinder section 32 of each pump piston 30 that has a smaller diameter than the remainder of pump piston 30. Hammerhead 28 defines the face side, connection side end of pump piston 30 and forms a counter-surface 34 to abutment surface 20.

As is illustrated in particular by FIG. 4, as transverse groove 36 branches off from an inwardly end of groove 26. Groove 26 accordingly together with transverse groove 36 forms a guide for a bayonet lock with the respective lug 16 to first perform an axial insertion motion which then comes to an end when lugs 16 abut against the inside lower end of grooves 26, to thereafter be pivoted in a pivotal motion into transverse groove 36 and thereby be axially locked. In the final position on the end side abutting transverse groove 36, a catch projection can be active which forms an anti-rotation lock between pump module 10 and drive casing 2 so that pump module 10 is secured in its final position.

Lugs 16 shown in FIG. 3 are not of identical configuration. Identical are instead only lugs 16.1 and 16.2 for which the associated grooves are formed adapted accordingly. Lug 16.4 is in its circumferential extension less wide than lugs 16.1 to 16.3. It is associated with a correspondingly narrow groove 26. Corresponding groove 26 accordingly fits together only with lug 16.4, whereby a unique orientation between pump module 10 and recess 8 is determined.

Figure 6C:
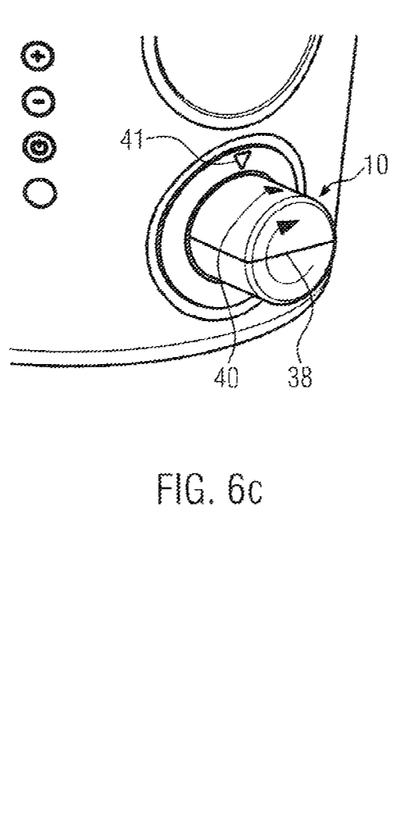
Figure 7:
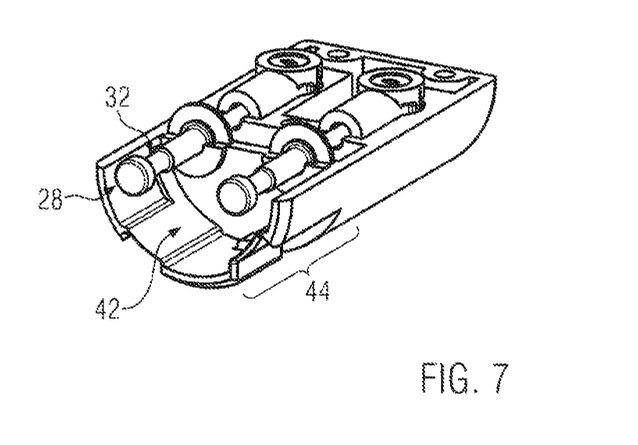
FIG. 7 shows a perspective partially transparent side view of the pump module of the embodiment.

Drawn in FIG. 4 is further a catch and switch projection 37 within transverse groove 36 which is exposed in transverse groove 36 and formed fixedly on pump casing 12. This catch and switch projection 37 is associated with a switch 39 provided centrically in lug 16.2. Switch 39 is preloaded in a radial direction inwardly relative to recess 8 and interacts accordingly with catch and switch projection 37. Only actuation of this switch by catch and switch projection 37 gives rise to the possibility of driving drive pusher 18. If pump module 10 is accordingly not connected in the prescribed manner to drive unit 1, then the drive unit can not be operated. In addition, drive casing 2 and pump casing 12 are provided with mutually associated, preferably electronic lock and key mechanisms. For example, an RFID tag can be provided on pump casing 12 which is recognized by a reading unit that is provided on drive casing 2. Only in the presence of a respective RFID tag is drive pusher 16 released by a logic unit provided in drive casing 2, FIGS. 6*a* to *c* illustrate the insertion of pump module 10 into recess 8. As already mentioned above, pump module 10 is first pivoted by 30° in the counterclockwise direction relative to the final position to make lugs 16 coincide with grooves 26 (see FIG. 6*a*). The pivoted position is visualized by a division plane that is provided between two casing elements forming pump casing 12. In this relative orientation, pump module 10 can now be inserted into recess 8. This axial insertion motion is guided by lugs 16 which engage in grooves 26 formed to correspond thereto, in the representation according to FIG. 6*b* this axial insertion, which is in FIG. 6*b* illustrated by a straight arrow, of pump casing 12 is completed. Pump casing 12 is now inserted fully into recess 8. Thereafter, the pump casing is pivoted by 30° in a clockwise direction, as indicated by the arrow in FIG. 6*c*. After this pivotal motion by 30°, pump module 10 has reached its final position. The final position is indicated to the user by a directional arrow 40 which is provided on the outer periphery of pump casing 2 and is in the final position aligned with a position indicator 41 provided on drive casing 2. The directional arrow also indicates the direction of insertion for pump casing 2 into recess 8.

As the previously discussed figures illustrate, drive pushers 18 are exposed within recess 8 but are covered entirely by the latter circumferentially and thereby cased in a protected manner. Only cylindrical recess 8 provides access to drive pushers 18.

Similarly, pump casing 2 comprises a pump recess 42 which is enclosed by a sleeve section 44 of pump casing 12 marked with reference numeral 44 and forms grooves 26, 36 on its outer circumferential surface. The pump pistons with their connection end project slightly axially beyond sleeve section 44, but are otherwise received within sleeve section 44 and accessible only axially through the opening of pump recess 42.

Figure 8A:
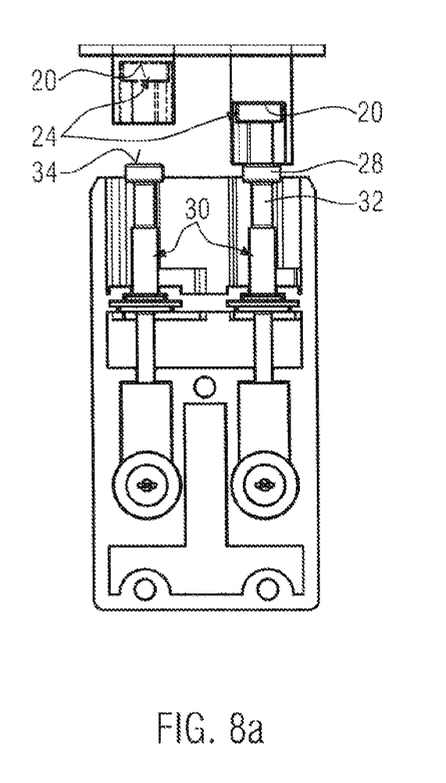
FIGS. 8a-d show semi-sectional views of the drive element and the drive counter-element of the embodiment and their position relative to each other during joining.
Figure 8B:
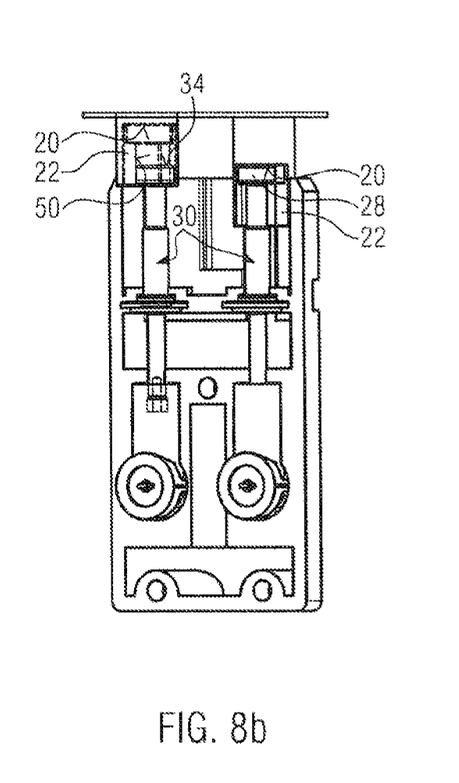
Figure 8C:
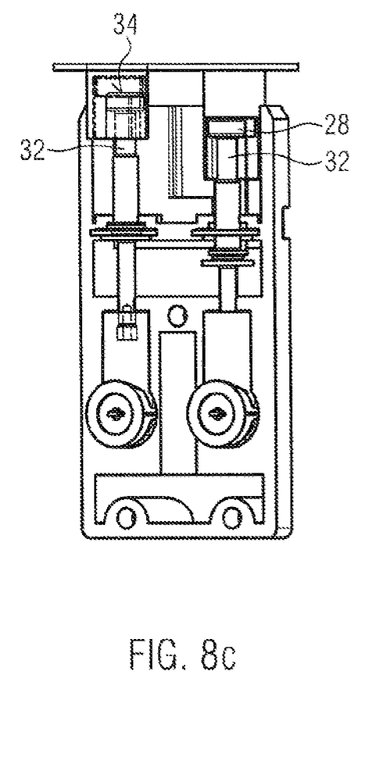
Figure 8D:
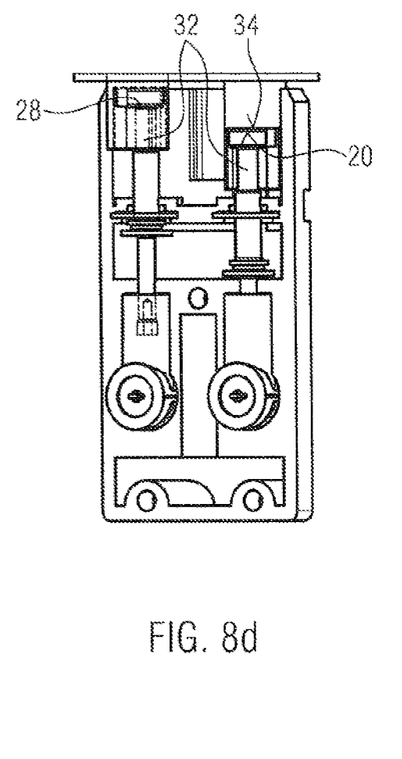

When joining pump casing 12 and drive casing 2, drive pushers 18 and pump pistons 30 are approached to each other, as is illustrate by FIGS. 8*a* and 8*b*. Due to the axial guidance of Jugs 16 in grooves 26, counter-surface 34 formed by hammerhead 28 is at least in part located above the abutment surface formed by drive pusher 18 (cf. FIG. 9*a*). A progressive axial motion ultimately causes pump piston 30 to bear with the end side against abutment surface 20, and even when the alternately axially moved drive pushers 18 project at different distances into recess 8, as this is implied by the representation of FIGS. 8*a* to *d*. With increasing proximity of pump casing 12 to drive casing 2, no further relative axial motion arises thereafter between the pair of drive element 18 and pump piston 30 shown in FIGS. 8*a* to *d* at the top. According to another axial displacement motion of pump casing 12 relative to drive casing 2 illustrated in FIGS. 8b, 8c and 8d, lower pump piston 30 finally with its counter-surface 34 finally abuts against abutment surface 20 of associated drive pusher 18.

The respective hammerhead 28 of the two pump pistons 30 is located in an eccentric position relative to the center of drive pusher 18, which is shown in FIG. 9a. Pump casing 12 is typically after the axial abutment of both pump pistons 30 against drive pushers 18 displaced by a further minor distance axially relative to drive casing 2, so that it is ensured that an axial abutment of pump piston 30 is always reliably achieved against drive pusher 18 until the axial final position has been reached when joining pump module 10 and drive casing 2, before pump module 10 is pivoted relative to the drive casing. The configuration is certainly to be such that reliable abutment of pump piston 30 against drive pusher 18 is after completion of the axial insertion motion obtained in every possible position of drive pusher 18, even in a position of drive pusher 18 being in the lowest position within recess 8.

Figure 9B:
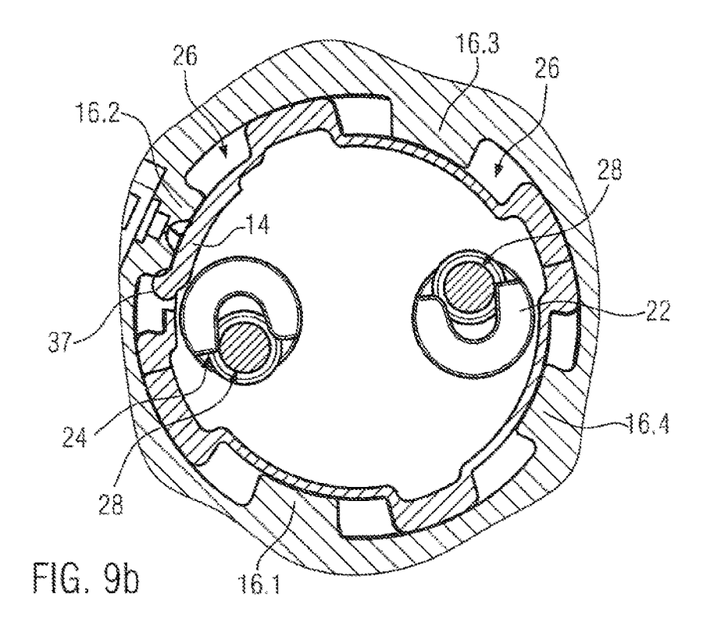
Figure 9C:
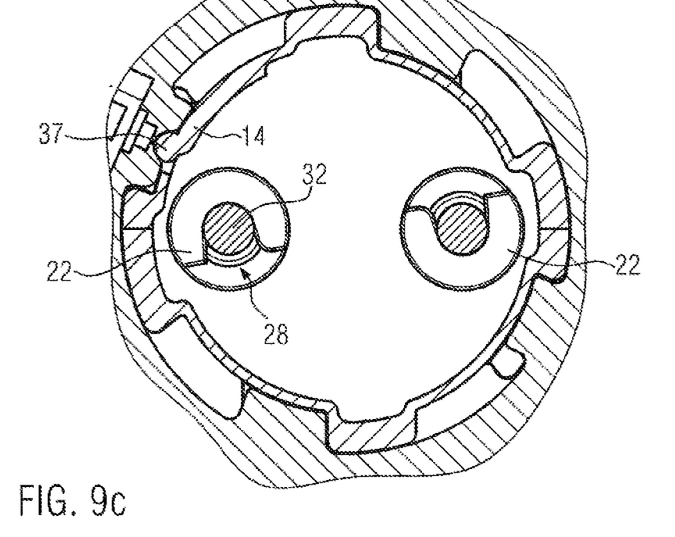

After this axial final position has been reached, pump module 10 is then pivoted clockwise. Hammerheads 28 being disposed eccentric to the center of this pivotal motion are thereby—as illustrated in FIGS. 9a to 9c—with their counter-surface 34 in a sliding, manner on abutment surface 20 displaced relative to drive pusher 18, namely in a plane extending perpendicular to the direction of insertion. The previously eccentric arrangement of pump pistons 30 relative to drive pushers 18 according to FIG. 9a via an intermediate position shown in FIG. 9b thereafter approaches the final position shown in FIG. 9c. In this final position, lugs 16 abut against stops which are farmed by transverse grooves 36. Pump casing 12 is commonly locked against drive casing 2. Pump pistons 30 are arranged substantially concentric to drive pushers 18. Each claw 22 engages over the associated hammerhead 28. Hammerhead 28 is by engagement of hammerhead seat 24 comprising claw 26 held in an axially positive-locking manner. Hammerhead seat 24 is typically matched axially exactly to the height of hammerhead 28 so that a play-free axial positive-locking connection between drive pusher 18 and pump piston 30 arises. As shown in FIGS. 9a-c, catch and switch projection 37 is located at a free end of a spring, arm 14 formed by pump casing 12 which snaps into a locking depression formed by lug 16.2 (cf. FIG. 9).

Detaching pump module 10 is done in the opposite direction. Here as well, respective hammerheads 28 are by pivoting first made to disengage from hammerhead seats 24. Pump module 10 can then be extracted from recess 18. This motion is guided by the interaction of lugs 16 with axial grooves 26.

Figure 10:
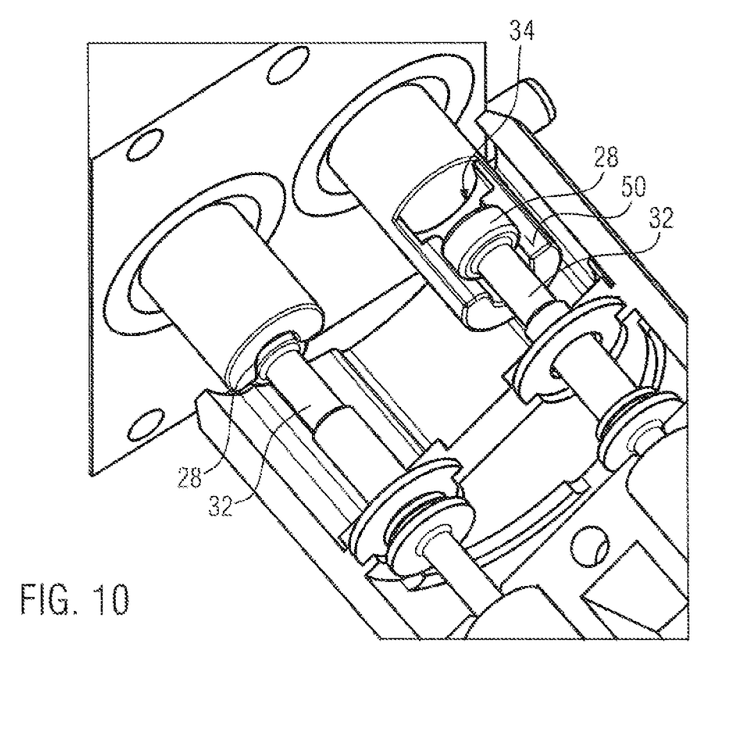
FIG. 10 shows a perspective partially transparent side view.

FIG. 10 illustrates a lock of the embodiment shown which prevents that the pivotal motion to the final position can be performed when hammerheads 28 are insufficiently engaged. Because claw 22 with its outer contour forms a stop 50 which acts radially, i.e. interacts with hammerhead 28 when pump casing 12 is pivoted, as shown in FIG. 10, and accordingly prevents a pivotal motion according to FIGS. 9a to 9c. Such pivotal motion can theoretically be possible when lugs 16 have reached the lower end of longitudinal grooves 26, i.e., when pump casing 12 is fully inserted into recess 8, a pump piston 30, however, is not held in the forwardly position projecting in the direction of drive casing 2, for example due to manual displacement of pump piston 30. Incorrect mounting of pump module 10 to drive casing 2 is accordingly avoided by this radial stop 50. This stop 50 is only active as long as hammerhead 28 is in the axial direction, i.e. the direction of insertion, located at the same height as stop 50, i.e. claw 22, and has not yet been moved to the level of hammerhead seat 24.

As is evident, hammerheads 28 are formed to be rotationally symmetrical. Pump piston 30 can then be supported freely rotatable at pump casing 12. In contrast, drive pushers 18 are mounted to drive casing 2 in a rotationally fixed manner so that the C-shaped opening of claws 22 is aligned such that the pivotal motion of pump module 10 relative to the final position due to the eccentric arrangement of drive pushers 18 and pump pistons 30 relative to the pivot axis of this pivotal motion, but with the same radius about this center, leads to a forced reception of cylinder sections 32 of respective pump pistons 30.

As it arises from the above general description, the drive unit has a rotationally symmetrical recess for receiving a likewise rotationally symmetrical cylindrical section which is in the specific embodiment formed by sleeve 44. This section 44 is basically received in the manner of a fitting within recess 8 and held thereby. Only positive-locking elements 16 or positive-locking counter-elements 26, 36, respectively, engage above or behind the cylindrical surface. Pump module 10 is there pivotally guided and supported within recess 8. The pivot axis of this pivotal motion there forms the center longitudinal axis of recess 8 or the center longitudinal axis of cylindrical section 44, respectively. Due to the eccentric arrangement of drive element 18 and drive counter-element (or pump piston) 30, respectively, relative to the center longitudinal axis and the relative arrangement of drive element 18 relative to drive counter-element (or pump piston) 30 after the axial final position has been reached and before pivoting for positively locking pump module 10 to drive casing 2, a forced positive-liquid coupling between drive element 18 and drive counter-element 30 in the frame work of the pivotal motion causes. Claw 22 of pump piston 30 configured as a drive device there forms the positive-locking mechanism of the drive unit. The positive-locking counter-mechanism provided for this is in the embodiment shown formed by hammerhead 28.

What is claimed is:

1. A device for producing a fluid jet for the removal of biological tissue, with a drive provided in a drive casing and a pump module comprising a pump casing, wherein said drive casing and said pump module can be detachably joined, wherein said drive casing comprises at least one positive-locking element and said pump casing comprises at least one positive-locking counter-element, wherein said positive-locking element when joining said pump module and said drive casing interacts with said positive-locking counter-element such that said pump casing is, until a final position has been reached in which said pump casing is connected to said drive casing and at least one drive element of the drive provided at said drive casing is connected to an associated drive counter-element of said pump module, imposed a pivotal motion relative to said drive casing, wherein said at least one drive element and said drive counter-element are arranged eccentric to a pivot axis of said pivotal motion and configured such that a positive-locking connection between said at least one drive element and said drive counter-element arises due to the pivotal motion;
   wherein at least one of said at least one drive element and said drive counter-element is arranged axially reciprocal and that said at least one drive element and said drive counter-element are configured such that said at least one drive element having an abutment surface abuts against a counter-surface of said drive counter-element before the final position has been reached;

wherein said at least one drive element is formed by a drive pusher which with its abutment surface abuts against a surface of a pump piston forming the counter-surface of said drive counter-element, before joining of said drive casing and said pump module in the axial direction is completed;

wherein one of said at least one drive element and said drive counter-element forms a hammerhead and the other of said at least one drive element and said drive counter-element forms a hammerhead seat adapted to engage over said hammerhead;

wherein said element forming said hammerhead seat is mounted in a rotationally-fixed manner; and wherein said hammerhead seat comprises a claw engaging in the final position axially over said hammer head, and wherein the drive element defines a radial stop for said hammerhead, which interacts with the hammerhead to prevent pivoting of the pump module to the final position.

2. The device according to claim 1, wherein said positive-locking element and said positive-locking counter-element form a bayonet lock which imposes upon said pump casing relative to said drive casing first an axial motion relative to a cylindrical recess and thereafter a pivotal motion extending perpendicular thereto.

3. The device according to claim 2, wherein said positive-locking element and said positive-locking counter-element are configured such that said pump casing is during joining and at the end of the axial motion relative to said drive casing pivotable by an angle of between 10° to 90°.

4. The device according to claim 2, said positive-locking element and said positive-locking counter-element are configured such that said pump casing is during joining and at the end of the axial motion relative to said drive casing pivotable by an angle of between 25° and 35°.

5. The device according to claim 1, wherein said drive casing forms a recess in which said drive element is exposed.

6. The device according to claim 5, wherein said recess, said pump casing, or both the recess and pump casing are at least in part configured to be rotationally symmetrical.

7. The device according to claim 1, wherein said pump casing forms a pump recess in which said drive counter-element is exposed and which is enclosed by a sleeve section of said pump casing which at least in part forms said positive-locking counter-element.

8. The device according to claim 1, wherein said positive-locking element and said positive-locking counter-element form a guide with which a unique orientation of said pump casing relative to said drive casing is defined, during joining.

9. A drive unit of a device for producing a fluid jet for the removal of biological tissue according to claim 1, wherein said drive is provided in said drive casing comprising at least one positive-locking element with which said pump module can be fixed to said drive casing and on which a recess is provided in which said drive element of said drive is exposed which is arranged eccentric relative to a center longitudinal axis of said recess and which comprises a positive-locking mechanism for coupling said drive element in a positive-locking manner to said drive counter-element by pivoting said pump module about the center longitudinal axis of said recess for fixing said pump module at said drive casing in a positive-locking manner.

10. A pump module of a device for producing a fluid jet for the removal of biological tissue according to claim 1, with said pump casing comprising at least one positive-locking counter-element with which said pump module can he fixed to said drive casing of said drive, and a cylindrical section adapted for being introduced into a recess of said drive casing, and with said drive counter-element which is arranged eccentric relative to a center longitudinal axis of said cylindrical section and a positive-locking counter-mechanism for coupling said drive counter-element in a positive-locking manner to said at least one drive element exposed in said recess by pivoting said pump module around the center longitudinal axis of said cylindrical section for fixing said pump module at said drive casing in a positive-locking manner.

* * * * *